United States Patent
Chandel et al.

(10) Patent No.: US 11,373,731 B2
(45) Date of Patent: Jun. 28, 2022

(54) SYSTEM AND METHOD TO CLASSIFY CARDIOPULMONARY FATIGUE

(71) Applicant: Tata Consultancy Services Limited, Mumbai (IN)

(72) Inventors: Vivek Chandel, Gurgaon (IN); Dhaval Satish Jani, Rockville, MD (US); Sundeep Khandelwal, Noida (IN); Shalini Mukhopadhyay, Kolkata (IN); Dibyanshu Jaiswal, Kolkata (IN); Avik Ghose, Kolkata (IN); Arpan Pal, Kolkata (IN); Kartik Muralidharan, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 909 days.

(21) Appl. No.: 16/179,784

(22) Filed: Nov. 2, 2018

(65) Prior Publication Data
US 2019/0138688 A1    May 9, 2019

(30) Foreign Application Priority Data
Nov. 4, 2017    (IN) .............................. 201721039348

(51) Int. Cl.
*G16B 40/00*    (2019.01)
*A61B 5/0205*    (2006.01)
(Continued)

(52) U.S. Cl.
CPC ............ *G16B 40/00* (2019.02); *A61B 5/0205* (2013.01); *A61B 5/02416* (2013.01);
(Continued)

(58) Field of Classification Search
CPC .............. A61B 5/0205; A61B 5/02416; A61B 5/02438; A61B 5/1118; A61B 5/6802; A61B 5/681; G16B 40/00; G16B 50/00
See application file for complete search history.

(56) References Cited

U.S. PATENT DOCUMENTS

| | | | |
|---|---|---|---|
| 8,808,188 B2* | 8/2014 | Banet | A61B 5/02125 600/490 |
| 2010/0179438 A1* | 7/2010 | Heneghan | A61B 5/113 600/595 |

(Continued)

FOREIGN PATENT DOCUMENTS

| | | |
|---|---|---|
| EP | 3219254 | 9/2017 |
| WO | WO-2015/101698 | 7/2015 |

OTHER PUBLICATIONS

Fusco, A. et al. "On how to extract breathing rate from PPG signal using wearable devices," *2015 IEEE Biomedical Circuits and Systems Conference (BioCAS)*, Oct. 22-24, 2015, Atlanta, GA; 5 pages.

*Primary Examiner* — Raymond S Dean
(74) *Attorney, Agent, or Firm* — Finnegan, Henderson, Farabow, Garrett & Dunner, LLP

(57) ABSTRACT

This disclosure relates generally to classification of cardiopulmonary fatigue. The method and system provides a longitudinal monitoring platform to classify cardiopulmonary fatigue of a subject using a wearable device worn by the subject. The activities of the subject is continuous monitored by plurality of sensors embedded in a wearable device. The received sensor signals are processed in multiple stages to classify cardiopulmonary fatigue as healthy or unhealthy based on respiratory, heart rate and recovery duration parameters extracted from the received sensor data. Further using (Continued)

the classified cardiopulmonary fatigue level, the C2P also performs longitudinal analysis to detect potential cardiopulmonary disorders.

10 Claims, 9 Drawing Sheets

(51) Int. Cl.
*A61B 5/00* (2006.01)
*A61B 5/024* (2006.01)
*A61B 5/11* (2006.01)
*G16B 50/00* (2019.01)

(52) U.S. Cl.
CPC ........ *A61B 5/02438* (2013.01); *A61B 5/1118* (2013.01); *A61B 5/681* (2013.01); *A61B 5/6802* (2013.01); *G16B 50/00* (2019.02)

(56) References Cited

U.S. PATENT DOCUMENTS

| | | | | |
|---|---|---|---|---|
| 2014/0221852 | A1* | 8/2014 | Van Slyke | A61B 5/7257 600/484 |
| 2016/0058318 | A1* | 3/2016 | Borjigin | A61B 5/318 600/521 |
| 2016/0094899 | A1* | 3/2016 | Aumer | A61B 5/6802 340/870.07 |
| 2016/0157776 | A1 | 6/2016 | Mestha et al. | |
| 2016/0249174 | A1* | 8/2016 | Patel | A61B 5/01 |
| 2016/0361020 | A1* | 12/2016 | LeBoeuf | A61B 5/7278 |
| 2016/0374625 | A1* | 12/2016 | Mulligan | A61B 5/4875 600/479 |
| 2017/0282011 | A1* | 10/2017 | Jang | A61B 5/02438 |
| 2018/0325385 | A1* | 11/2018 | Deterding | A61B 5/14551 |

\* cited by examiner

SYSTEM AND METHOD TO CLASSIFY CARDIOPULMONARY FATIGUE

CROSS-REFERENCE TO RELATED APPLICATIONS AND PRIORITY

The present application claims priority from Indian provisional specification no. 201721039348 filed on 4 Nov. 2017, the complete disclosure of which, in its entirety is herein incorporated by references.

TECHNICAL FIELD

The disclosure herein generally relates to field of cardiopulmonary fatigue and, more particularly, to classification of cardiopulmonary fatigue.

BACKGROUND

Cardiopulmonary disorders affect normal functioning of heart and lungs. The key contributors of the cardiopulmonary disorders are unhealthy eating habits and work environments. The cardiopulmonary diseases may be prevented by early detection and diagnosis of symptoms of the cardiopulmonary disorders. One of the commonly encountered symptoms of cardiopulmonary disorder is fatigue.

Fatigue is a frequent complaint encountered with cardio diseases like heart failure, valvular heart diseases, cardiomyopathies, coronary artery disease. Fatigue is caused by abnormal stress, wherein abnormal stress is caused due to short spells of intensive activities in routine jobs like walking on stairs, brisk walking and so on. Hence while a subject is unobtrusively involved in activities, he may provide signs for any possible detection of cardiopulmonary disorder at an early stage.

Conventional clinical tools for detecting cardiopulmonary fatigue or stress level, require a subject to be monitored under supervision of an expert in a lab. The existing clinical tools use various parameters of a subject such as Heart Rate (HR), Breathing Rate (BR) to monitor health status of a subject, wherein the focus is on heart rate estimation rather than respiration monitoring. However, respiration monitoring is equally critical as power spectrum or scaled power of breathing/respiration state of a subject before and after activity is substantially different and also results in more efficient estimation, when continuously monitored. Further for monitoring information recorded continuously over a period of time, frequent lab visits can be tedious, but can be reduced by introducing wearable devices such as smart watch, smart bands and so on for continuously collecting and monitoring respiration and heart rate of a subject to enable effective detection of cardiopulmonary fatigue that further detects potential symptoms of cardiopulmonary disorders.

SUMMARY

Embodiments of the present disclosure present technological improvements as solutions to one or more of the above-mentioned technical problems recognized by the inventors in conventional systems. For example, in one embodiment, a method and system to classify cardiopulmonary fatigue is provided. The proposed method and system is a Cardiopulmonary Care Platform (C2P) that classifies cardiopulmonary fatigue level of a subject as healthy or unhealthy by analyzing sensor signal received from a subject using a wearable device worn by the subject. The received sensor signals is processed to classify cardiopulmonary fatigue as healthy or unhealthy based on respiratory, heart rate and recovery duration parameters extracted from the received sensor data. Further using the classified cardiopulmonary fatigue level, the C2P also performs longitudinal analysis to detect potential cardiopulmonary disorders.

In another aspect, a method to classify cardiopulmonary fatigue is provided. The method includes sensing a plurality of physiological data from the subject using a plurality of physiological sensors while the subject is performing an activity. Further the method includes detecting a set of activity parameters using a plurality of activity detectors and extracting initial heart rate (HR), breathing rate (BR) and breathing signal power (BP) from the sensed plurality of physiological data. Furthermore, the method includes obtaining metabolic equivalent (MET) values from a MET database based on the activity performed by the subject during a pre-defined time interval, wherein the database stores MET values of multiple activities and estimating activity intensity (AI) of the subject for the pre-defined time interval based on the MET values and the subject data. Further the method includes estimating an expected value of HR, BR and BP based on estimated AI, initial HR, BR, BP and their respective pre-determined normalizing constant and further estimating an expected recovery duration (RD) based on estimated AI and its respective normalizing constant. Further the method includes extracting actual HR, BR and BP from sensed plurality of physiological data at the end of the activity performed by the subject and estimating an actual recovery duration (RD) depending on the duration taken by the subject for recovery. Further the method includes computing difference values between actual HR, BR, BP, RD and respective expected values of HR, BR, BP and RD. Further the method includes estimating a deviation factor based on the computed difference values and a pre-determined normalizing constant. Finally the method includes classifying the subject's fatigue as healthy or unhealthy fatigue based on the comparison of the deviation factor with a pre-determined standard value.

In another aspect, a system to classify cardiopulmonary fatigue is provided. The system comprises a memory storing instructions and a centralized database, one or more communication interfaces; and one or more hardware processors coupled to the memory via the one or more communication interfaces, wherein the one or more hardware processors are configured by instructions to: includes a pre-processing module a plurality of physiological sensors and a plurality of activity detectors in wearable device for sensing a plurality of physiological data and detection of activity performed from the subject. The system further includes a physiological data extractor for extracting initial heart rate (HR), breathing rate (BR) and breathing signal power (BP) from the sensed plurality of physiological data. Furthermore the system includes a MET obtaining module for obtaining metabolic equivalent (MET) values from a MET database based on the activity performed by the subject during a pre-defined time interval, wherein the database stores MET values of multiple activities. Further the system includes an activity intensity estimator for estimating activity intensity (AI) of the subject for the pre-defined time interval based on the MET values and the subject data and an expected value estimator for estimating an expected value of HR, BR and BP based on estimated AI, initial HR, BR, BP and their respective pre-determined normalizing constant. Furthermore the system includes an expected RD value estimator for estimating an expected recovery duration (RD) based on estimated AI and its respective normalizing constant. Further the system includes an actual value estimator for extracting actual HR, BR and BP from sensed plurality of physiological data at the end of the activity performed by the subject. Furthermore the system includes an actual RD value estimator for estimating an actual recovery duration (RD) depending on the duration taken by the subject for recovery. Further the system includes a difference estimator for estimating difference values between actual HR, BR, BP, RD and respective expected values of HR, BR, BP and RD. Furthermore the system includes a deviation estimator for estimating a deviation factor based on the computed difference values and a pre-demined normalizing constant. Furthermore the system includes a classification module for classifying the subject's fatigue as healthy or unhealthy fatigue based on the comparison of the deviation factor with a pre-determined standard value on the input/output interfaces. Finally the system comprises a longitudinal assessment module that is configured to performing longitudinal assessment of estimated AI, nature of fatigue caused, and physiological sensor data for several months to detect any underlying cardiopulmonary disorder.

In yet another aspect, a non-transitory computer readable medium to classify cardiopulmonary fatigue is provided. The method includes sensing a plurality of physiological data from the subject using a plurality of physiological sensors while the subject is performing an activity. Further the method includes detecting a set of activity parameters using a plurality of activity detectors and extracting initial heart rate (HR), breathing rate (BR) and breathing signal power (BP) from the sensed plurality of physiological data. Furthermore, the method includes obtaining metabolic equivalent (MET) values from a MET database based on the activity performed by the subject during a pre-defined time interval, wherein the database stores MET values of multiple activities and estimating activity intensity (AI) of the subject for the pre-defined time interval based on the MET values and the subject data. Further the method includes estimating an expected value of HR, BR and BP based on estimated AI, initial HR, BR, BP and their respective pre-determined normalizing constant and further estimating an expected recovery duration (RD) based on estimated AI and its respective normalizing constant. Further the method includes extracting actual HR, BR and BP from sensed plurality of physiological data at the end of the activity performed by the subject and estimating an actual recovery duration (RD) depending on the duration taken by the subject for recovery. Further the method includes computing difference values between actual HR, BR, BP, RD and respective expected values of HR, BR, BP and RD. Further the method includes estimating a deviation factor based on the computed difference values and a pre-determined normalizing constant. Finally the method includes classifying the subject's fatigue as healthy or unhealthy fatigue based on the comparison of the deviation factor with a pre-determined standard value.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 7A:
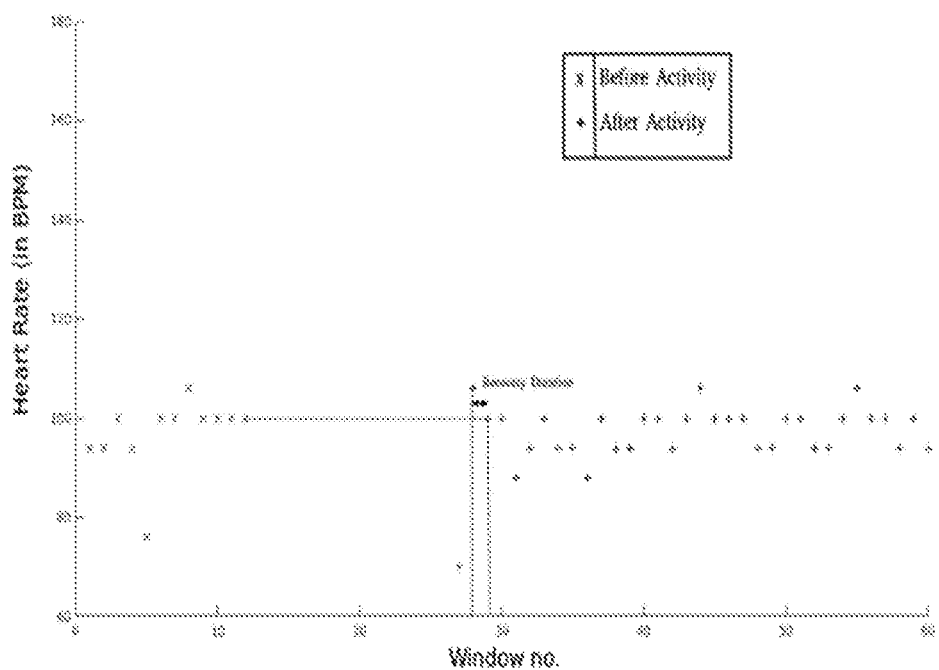
FIGS. 7A and 7B illustrates before activity and after activity graphs of low recovery duration (RD), according to some embodiments of the present disclosure.
Figure 7B:
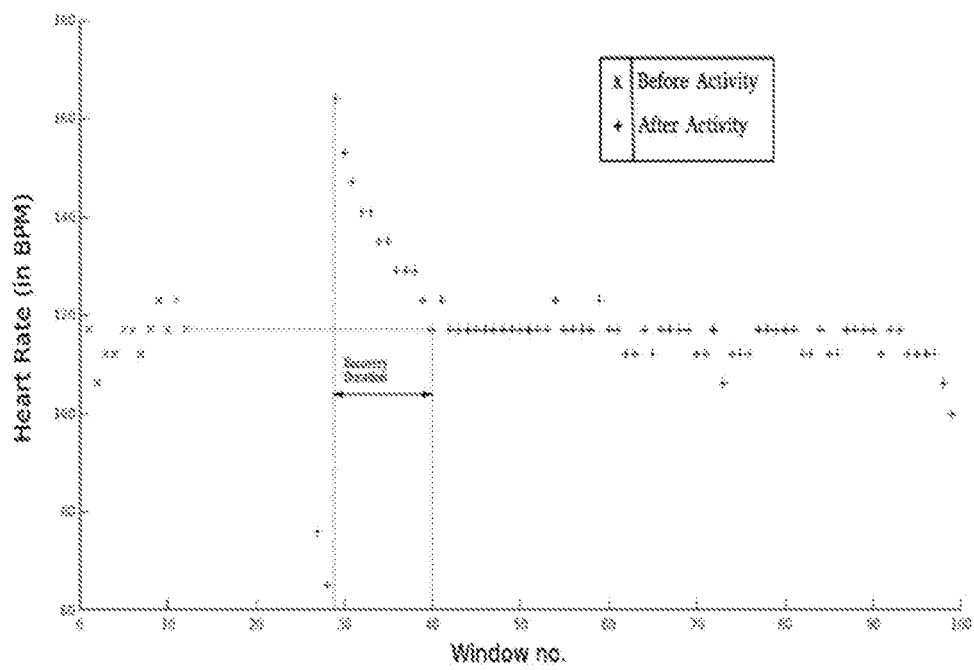

Referring now to the drawings, and more particularly to FIG. through FIG. 7B, where similar reference characters denote corresponding features consistently throughout the figures, there are shown preferred embodiments and these embodiments are described in the context of the following exemplary system and/or method.

Figure 1:
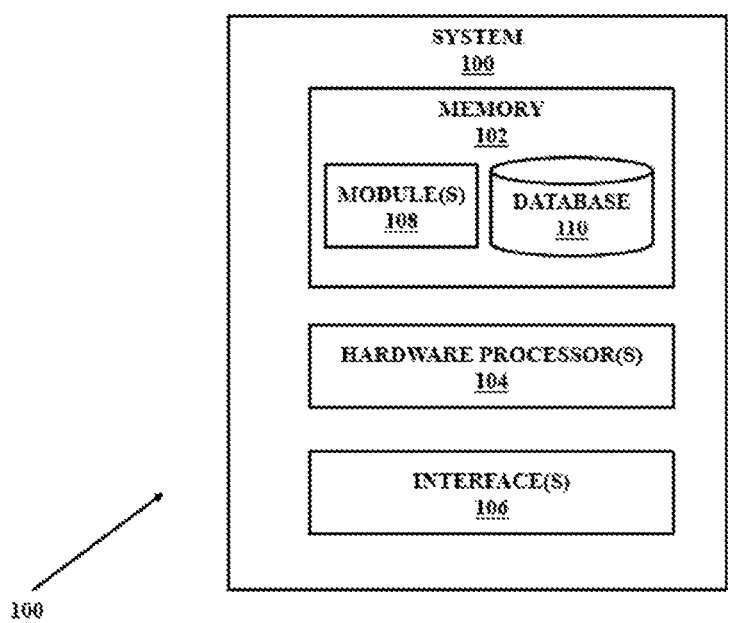
FIG. 1 illustrates an exemplary block diagram of a system to classify cardiopulmonary fatigue in accordance with some embodiments of the present disclosure.

FIG. 1 illustrates an exemplary block diagram of a system 100 to classify cardiopulmonary fatigue according to an embodiment of the present disclosure. In an embodiment, the system 100 includes memory 102, one or more hardware processors 104, communication interface device(s) or input/output (I/O) interface(s) 106, and one or more data storage devices or memory 102 operatively coupled to the one or more processors 104. The memory 102 comprises one or more modules 108 and the database 110. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical subject interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
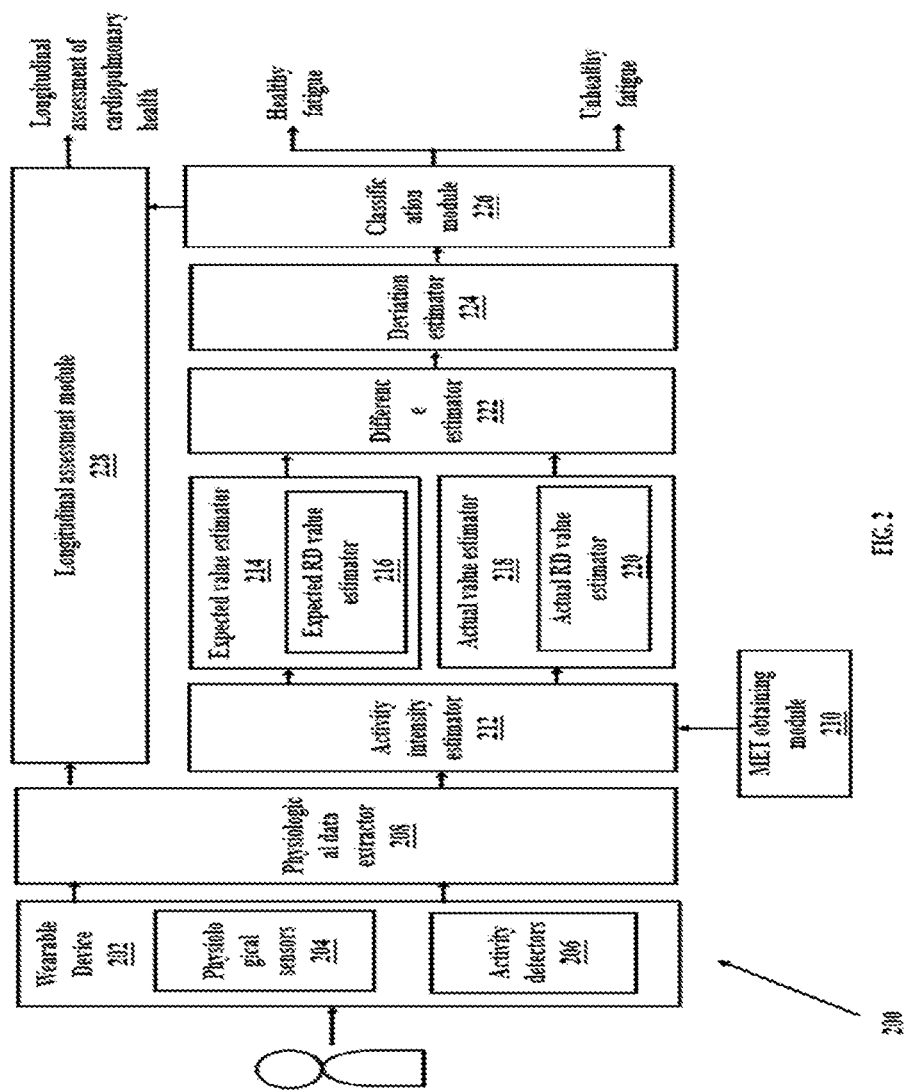
FIG. 2 is a functional block diagram of various modules stored in module(s) of a memory of the system of FIG. 1 in accordance with some embodiments of the present disclosure.

FIG. 2, with reference to FIG. 1, is a block diagram of various modules 108 stored in the memory 102 of the system 100 of FIG. 1 in accordance with an embodiment of the present disclosure. In an embodiment of the present disclosure, the system 100 comprises a wearable device (202) that further comprises of plurality of physiological sensors (204) and a plurality of activity detectors (206) in for sensing a plurality of physiological data and detecting a set of activity parameters respectively from a subject using while the subject is performing an activity. Further the system 100 includes a physiological data extractor (208) for extracting initial heart rate (HR), breathing rate (BR) and breathing signal power (BP) from the sensed plurality of physiological data. The system 100 further includes a MET obtaining module (210) for obtaining metabolic equivalent (MET) values. Further the system 100 includes an activity intensity estimator (212) for estimating activity intensity (AI) of the subject. Further the system 100 includes an expected value estimator (214) and an expected RD value estimator (216) for estimating an expected value of HR, BR and BP and for estimating an expected recovery duration (RD) respectively. Further the system 100 includes an actual value estimator (218) and an actual RD value estimator (220) for extracting actual HR, BR and BP and for estimating an actual recovery duration (RD) respectively. The system 100 further includes a difference estimator (222) for estimating difference values between actual HR, BR, BP, RD and respective expected values of HR, BR, BP and RD. Further the system comprises of a deviation estimator (224) for estimating a deviation and finally a classification module (226) for classifying the subject's fatigue as healthy or unhealthy fatigue based on the comparison of the deviation factor with a pre-determined standard value on the input/output interfaces that are implemented as at least one of a logically self-contained part of a software program, a self-contained hardware component, and/or, a self-contained hardware component with a logically self-contained part of a software program embedded into each of the hardware component that when executed perform the above method described herein.

According to an embodiment of the disclosure, the system 100 comprises the wearable device (202) that further comprises of plurality of physiological sensors (204) and a plurality of activity detectors (206) in for sensing a plurality of physiological data and detecting a set of activity parameters respectively from a subject using while the subject is performing an activity.

In an embodiment, the plurality of physiological sensors (204) sense physiological signals from the subject that includes photoplethysmogram (PPG) signals. The PPG signals are sensed at multiple time intervals including rest time and activity time of the subject. Further a set of activity parameters are detected using a plurality of activity detectors (206) present on a non-intrusive wearable device (202) attached to the subject. The activity detectors (206) further comprise of a plurality of sensors that include inertial measurement unit (IMU), pressure sensor. The activity detectors (206) continuously monitors and detects any activity performed by the subject that includes brisk walking, moving up/down stairs, cycling.

According to an embodiment of the disclosure, the system 100 further comprises the physiological data extractor (208) that is configured to extract initial heart rate (HR), breathing rate (BR) and breathing signal power (BP) from the sensed plurality of physiological data. The sensor signals that include PPG signals are processed to extract physiological features like complete breathing cycles that include breathing rate (BR) and breathing signal power (BP), and heart rate (HR) using techniques known in art such as Fourier Transform based techniques to obtain Power Spectral Density of signals filtered in respective frequency ranges of the BR, BP and HR.

According to an embodiment of the disclosure, the system 100 further comprises the MET obtaining module (210) that provides an exhaustive list of a metabolic equivalent (MET) values for activity performed by the subject. The MET obtaining module (210) obtains MET values from a database that stores MET values of multiple activities. The MET values are obtained for a pre-defined time interval, such as while performing activity, wherein time ($t_b$ denotes time while activity begins and time ($t_e$ denotes time while activity ends.

According to an embodiment of the disclosure, the system 100 further comprises the activity intensity estimator (212) that estimates activity intensity (AI) of the subject for the pre-defined time interval based on the MET values and the subject data. Activity Intensity (AI) of the subject is estimated based on MET and user profile data, that includes subject's body weight (W), a pre-defined time interval (T), the subject's level of physical activity in daily life (LPA), gender (G), age (A) and pre-determined normalization constant 'N', which is expressed as follows;

$$I = f_i(MET, W, T, LPA, G, A, N) \quad (1)$$

Where
W is subject's body weight
T is pre-defined time interval
LPA is level of physical activity in daily life of the subject
G is subject's gender
A is subject's age and
N is pre-determined normalization constant According to an embodiment of the disclosure, the system 100 further comprises the expected value estimator (214) that is configured to estimate an expected value of HR, BR and BP. The expected value of HR, BR and BP are estimated based on AI, initial HR, BR, BP and their respective pre-determined normalizing constant, which is expressed as shown below;

$$HR_f = f_{hr}(HR_i, I, N_{HR}) \quad (2)$$

$$BR_f = f_{br}(BR_i, I, N_{RR}) \quad (3)$$

$$BP_f = f_{bp}(BP_i, I, N_{BP}) \quad (4)$$

Where
$HR_f$ is expected HR
$BR_f$ is expected BR
$BP_f$ is expected BP f and I denote after and before time interval respectively
N$_{HR}$, N$_{BR}$ and N$_{BP}$ is pre-determined normalizing constant According to an embodiment of the disclosure, the system 100 further comprises the expected RD value estimator (216) that is configured to estimate an expected recovery duration (RD). The recovery duration (RD) is the time taken by the subject to reach a baseline heart rate after the end of the activity, wherein the baseline heart rate is basal heart rate of the subject at rest. The expected recovery duration (RD) is estimated depending on the duration taken by the subject for recovery after performing an activity, which is expressed as shown below;

$$RD_f = f_{rd}(I, N_{RD}) \quad (5)$$

Where
RD$_f$ is expected RD
f and I denote after and before time interval respectively
N$_{RD}$ is pre-determined normalizing constant According to an embodiment of the disclosure, the system 100 further comprises the actual value estimator (218) that is configured to estimate an actual HR, BR and BP from sensed plurality of physiological data at the end of the activity performed by the subject. The actual HR, BR and BP are denoted as HR$_a$, BR$_a$ and BP$_a$.

According to an embodiment of the disclosure, the system 100 further comprises the actual RD value estimator (220) that is configured to estimate an actual recovery duration (RD) at the end of the activity performed by the subject. The actual RD is denoted as RD$_a$.

According to an embodiment of the disclosure, the system 100 further comprises the difference estimator (222) that is configured to estimate difference values between actual HR, BR, BP, RD and respective expected values of HR, BR, BP and RD, which is expressed as shown below;

$$HR_d = HR_a - HR_f \quad (6)$$

$$BR_d = BR_a - BR_f \quad (7)$$

$$BP_d = BP_a - BP_f \quad (8)$$

$$RD_d = RD_a - RD_f \quad (9)$$

According to an embodiment of the disclosure, the system 100 further comprises the deviation estimator (224) that is configured to estimate a deviation factor based on the computed difference values and a pre-determined normalizing constant.

$$DF = f_d(HR_d, BR_d, BP_d, RD_d, N_d) \quad (10)$$

Where
f$_d$ is a norm function.
DF can also be alternatively expressed as shown below;

$$DF = \sqrt{(N_1 \times HR_d)^2 + (N_2 \times BR_d)^2 + (N_3 \times BP_d)^2 + (N_4 \times RD_d)^2} \quad (11)$$

According to an embodiment of the disclosure, the system 100 further comprises the classification module (226) that is configured to classify a subject's cardiopulmonary fatigue as healthy or unhealthy cardiopulmonary fatigue. The classification of cardiopulmonary fatigue is based on the comparison of the deviation factor with a pre-determined standard value. Further the classified cardiopulmonary fatigue is displayed on input/output (I/O) interface (106).

According to an embodiment of the disclosure, the system 100 further comprises the longitudinal assessment module (228) that is configured to performing longitudinal assessment of estimated AI, nature of fatigue caused, and physiological sensor data for several months to detect any underlying cardiopulmonary disorder. The longitudinal assessment module can be used by any medical expert to track health of any subject over a period of time by monitoring the patterns of detected cardiopulmonary fatigue caused to the subject owing to different activities performed in routine life, which may detect any potential cardiopulmonary disorder.

Figure 3A:
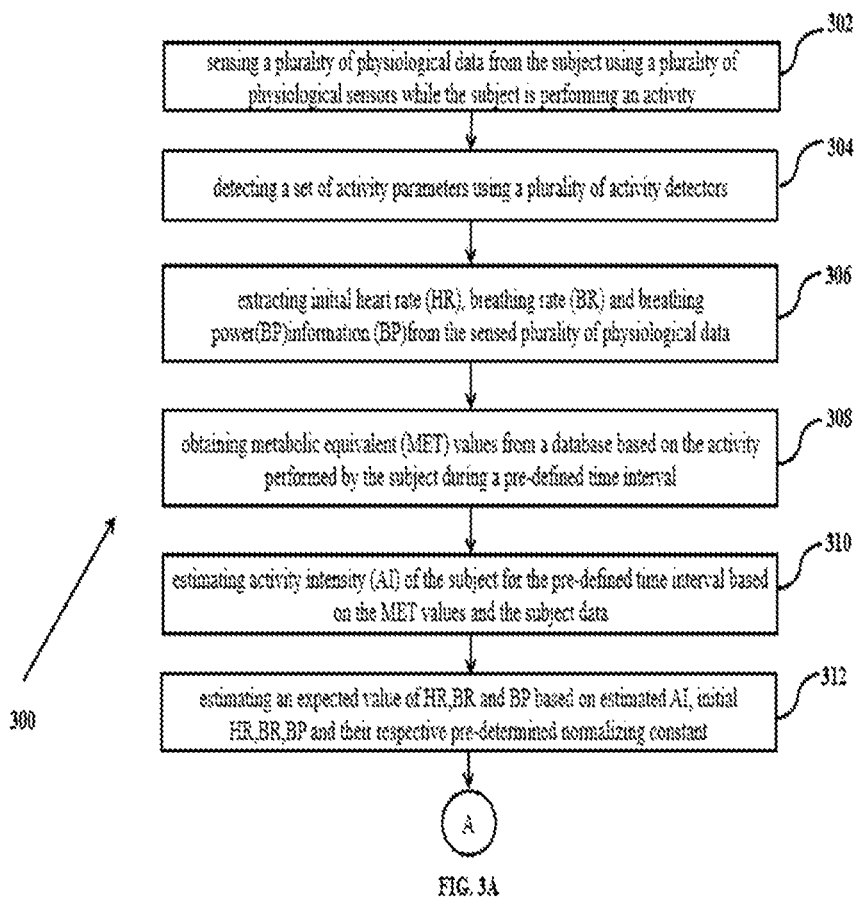
FIGS. 3A and 3B is an exemplary flow diagram illustrating a method to classify cardiopulmonary fatigue using the system of FIG. 1 in accordance with some embodiments of the present disclosure.
Figure 3B:
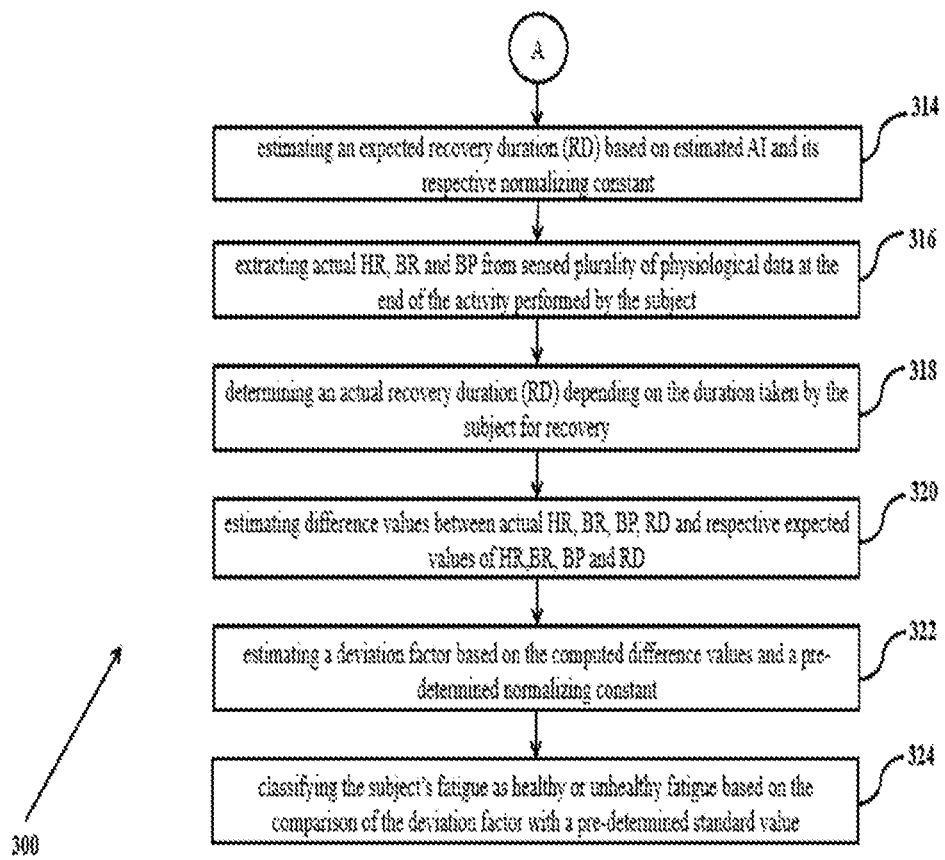

FIGS. 3A and 3B, with reference to FIGS. 1-2, is an exemplary flow diagram illustrating a method to classify cardiopulmonary fatigue using the system 100 of FIG. 1 according to an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 and the modules 302-324 as depicted in FIGS. 1-2, and the flow diagram as depicted in FIGS. 3A and 3B.

At step 302, a plurality of physiological data are sensed from a subject using the plurality of physiological sensors (204) while the subject is performing an activity. The plurality of physiological sensors are present on the non-intrusive wearable device (202) attached to the subject. The plurality of physiological sensors (204) sense physiological signals from the subject that includes photoplethysmogram (PPG) signals. The PPG signals are sensed at multiple time intervals including rest time and activity time of the subject.

In the next step at 304, a set of activity parameters are detected using the plurality of activity detectors (206). The plurality of activity detectors (206) are present on a non-intrusive wearable device (202) attached to the subject. The activity detectors (206) further comprise of a plurality of sensors that include inertial measurement unit (IMU), pressure sensor. The activity detectors (206) continuously monitors and detects any activity performed by the subject that includes brisk walking, moving up/down stairs, cycling.

In the next step at 306, initial heart rate (HR), breathing rate (BR) and breathing signal power (BP) are extracted from the sensed plurality of physiological data by the physiological data extractor (208). The sensor signals that include PPG signals are processed to extract physiological features like complete breathing cycles that include breathing rate (BR) and breathing signal power (BP), and heart rate (HR) using techniques known in art such as Fourier Transform based techniques to obtain Power Spectral Density of signals filtered in respective frequency ranges of the BR, BP and HR.

In the next step at 308, metabolic equivalent (MET) values for activity performed by the subject is obtained from the MET obtaining module (210). The MET obtaining module (210) obtains MET values from a database that stores MET values of multiple activities. The MET values are obtained for a pre-defined time interval, such as while performing activity, wherein time (t$_b$) denotes time while activity begins and time (t$_e$) denotes time while activity ends.

In the next step at 310, activity intensity (AI) of the subject is estimated for the pre-defined time interval based on the MET values and the subject data in the activity intensity estimator (212). Activity Intensity (AI) of the subject is estimated based on MET and user profile data, that includes subject's body weight (W), the pre-defined time interval (T), subject's level of physical activity in daily life (LPA), gender (G), age (A) and pre-determined normalization constant ('N').

In the next step at 312, an expected value of HR, BR and BP is estimated in the expected value estimator (214). The expected value of HR, BR and BP are estimated based on AI, initial HR, BR, BP and their respective pre-determined normalizing constant.

In the next step at 314, an expected recovery duration (RD) is estimated the expected RD value estimator (216). The recovery duration (RD) is the time taken by the subject to reach a baseline heart rate after the end of the activity, wherein the baseline heart rate is basal heart rate of the subject at rest. The expected recovery duration (RD) is estimated depending on the duration taken by the subject for recovery after performing an activity.

In the next step at 316, actual HR, BR and BP are extracting from sensed plurality of physiological data at the end of the activity performed by the subject the actual value estimator (218).

In the next step at 318, an actual recovery duration (RD) is estimated depending on the duration taken by the subject for recovery in the actual RD value estimator (220).

In the next step at 320, difference values between actual HR, BR, BP, RD and respective expected values of HR, BR, BP and RD is computed in the difference estimator (222).

In the next step at 320, a deviation factor is estimated based on the computed difference values and a pre-determined normalizing constant in the deviation estimator (224).

In the next step at 322, subject's cardiopulmonary fatigue is classified as healthy or unhealthy cardiopulmonary fatigue based on the comparison of the deviation factor with a pre-determined standard value in the classification module (226). Further the classified cardiopulmonary fatigue is displayed on input/output (I/O) interface (106).

Figure 4:
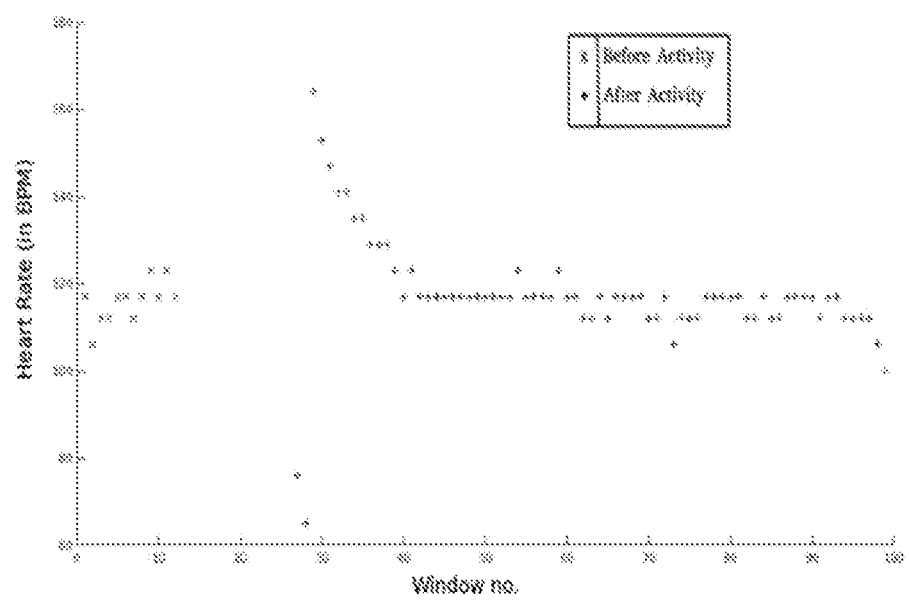
FIG. 4 illustrates before activity and after activity graphs of heart rate (HR), according to some embodiments of the present disclosure.

FIG. 4 illustrates before activity and after activity graphs of heart rate (HR), according to some embodiments of the present disclosure. In an embodiment, the graph illustrates the heart rate (HR) before and after activity, which is plotted on Y-Axis with respect a window of time interval on X-Axis.

Figure 5:
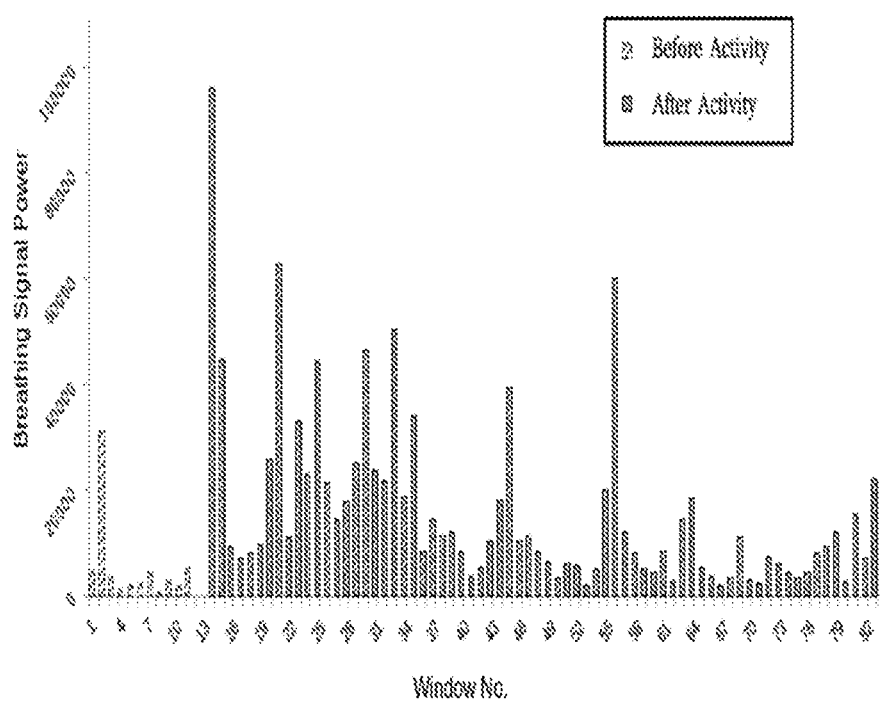
FIG. 5 illustrates before activity and after activity graphs of breathing signal power (BP), according to some embodiments of the present disclosure.

FIG. 5 illustrates before activity and after activity graphs of breathing signal power (BP), according to some embodiments of the present disclosure. In an embodiment, the graph illustrates the breathing signal power (BP) before and after activity, which is plotted on Y-Axis with respect a window of time interval on X-Axis.

Figure 6:
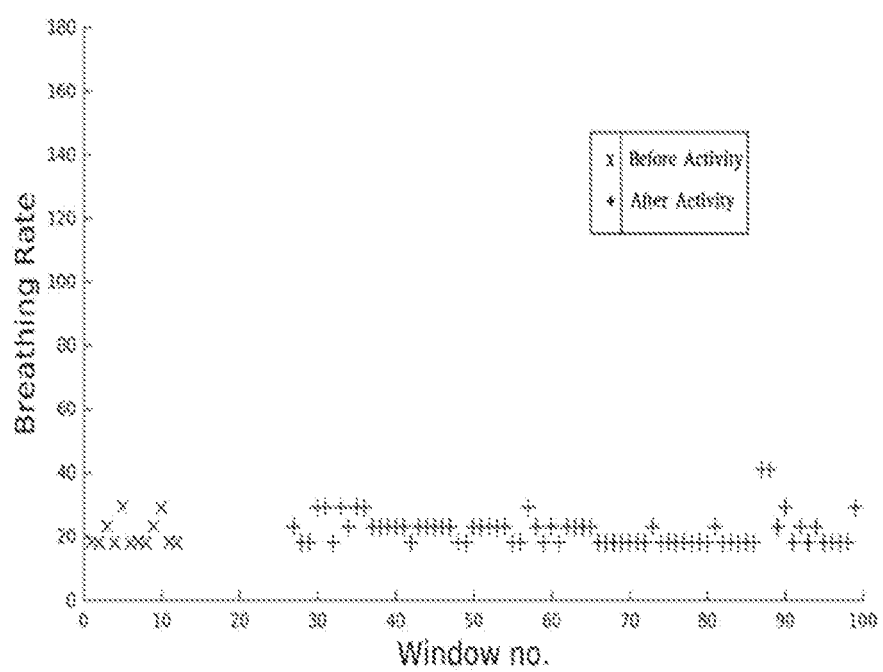
FIG. 6 illustrates before activity and after activity graphs of breathing rate (BR), according to some embodiments of the present disclosure.

FIG. 6 illustrates before activity and after activity graphs of breathing rate (BR), according to some embodiments of the present disclosure. In an embodiment, the graph illustrates the breathing rate (BR) before and after activity, which is plotted on Y-Axis with respect a window of time interval on X-Axis.

FIGS. 7A and 7B illustrates before activity and after activity graphs of recovery duration (RD), according to some embodiments of the present disclosure. In an embodiment, the graph illustrates the recovery duration (RD) recovery duration (RD), before and after activity, which is plotted on Y-Axis with respect a window of time interval on X-Axis.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Hence a method and a system to classify cardiopulmonary fatigue is provided. The proposed method and system is a Cardiopulmonary Care Platform (C2P) that classifies cardiopulmonary fatigue level of a subject as healthy or unhealthy by analyzing sensor signal received from a subject using a wearable device worn by the subject. The received sensor signals is processed to classify cardiopulmonary fatigue as healthy or unhealthy based on respiratory, heart rate and recovery duration parameters extracted from the received sensor data. Further using the classified cardiopulmonary fatigue level, the C2P also performs longitudinal analysis to detect potential cardiopulmonary disorders.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method to classify cardiopulmonary fatigue of a subject, the method comprising:
    sensing a plurality of physiological data from the subject using a plurality of physiological sensors while the subject is performing an activity (302);
    detecting a set of activity parameters using a plurality of activity detectors (304);
    extracting initial heart rate (HR), breathing rate (BR) and breathing signal power (BP) from the sensed plurality of physiological data (306);
    obtaining metabolic equivalent (MET) values from a MET database based on the activity performed by the subject during a pre-defined time interval, wherein the database stores MET values of multiple activities (308);
    estimating activity intensity (AI) of the subject for the pre-defined time interval based on the MET values and the subject data (310);
    estimating an expected value of HR, BR and BP based on estimated AI, initial HR, BR, BP and their respective pre-determined normalizing constant (312);
    estimating an expected recovery duration (RD) based on estimated AI and its respective normalizing constant (314);
    extracting actual HR, BR and BP from sensed plurality of physiological data at the end of the activity performed by the subject (316);
    estimating an actual recovery duration (RD) depending on the duration taken by the subject for recovery (318);
    computing difference values between actual HR, BR, BP, RD and respective expected values of HR, BR, BP and RD (320);
    estimating a deviation factor based on the computed difference values and a pre-determined normalizing constant (322);
    classifying the subject's fatigue as healthy or unhealthy fatigue based on the comparison of the deviation factor with a pre-determined standard value (324).

2. The method of claim 1, wherein the plurality of physiological sensors and activity detectors are present on a non-intrusive wearable device attached to the subject.

3. The method of claim 1 wherein the plurality of physiological sensor data includes photoplethysmogram (PPG) sensed at multiple time intervals including rest time and activity time of the subject.

4. The method of claim 1 includes estimating Activity Intensity (AI) of the subject based on MET and user profile data, that includes subject's body weight (W), a pre-defined time interval (T), subject's level of physical activity in daily life (LPA), gender (G), age (A) and pre-determined normalization constant ('N').

5. The method of claim 1, where in the recovery duration (RD) is the time taken by the subject to reach a baseline heart rate after the end of the activity, wherein the baseline heart rate is basal heart rate of the subject at rest.

6. The method of claim 1 further comprising the step of displaying subject's activity as healthy or unhealthy fatigue on an input/output (I/O) interface.

7. The method of claim 1 further comprising the step of performing longitudinal assessment of estimated AI, nature of fatigue caused, and physiological sensor data over several months to detect any underlying cardiopulmonary disorder.

8. A system to classify cardiopulmonary fatigue of a subject, comprising:
    a memory (102) storing instructions and one or more modules (108);
    a database (110);
    one or more communication or input/output interfaces (106); and
    one or more hardware processors (104) coupled to the memory (102) via the one or more communication interfaces (106), wherein the one or more hardware processors (104) are configured by the instructions to execute the one or more modules (108) comprising:
        a plurality of physiological sensors (204) in wearable device (202) for sensing a plurality of physiological data from the subject using while the subject is performing an activity;
        a plurality of activity detectors (206) in wearable device (202) detecting a set of activity parameters;
        a physiological data extractor (208) for extracting initial heart rate (HR), breathing rate (BR) and breathing signal power (BP) information (BP) from the sensed plurality of physiological data;
        a MET obtaining module (210) for obtaining metabolic equivalent (MET) values from a MET database based on the activity performed by the subject during a pre-defined time interval, wherein the database stores MET values of multiple activities;
        an activity intensity estimator (212) for estimating activity intensity (AI) of the subject for the pre-defined time interval based on the MET values and the subject data;
        an expected value estimator (214) for estimating an expected value of HR, BR and BP based on estimated AI, initial HR, BR, BP and their respective pre-determined normalizing constant;
        an expected RD value estimator (216) for estimating an expected recovery duration (RD) based on estimated AI and its respective normalizing constant;
        an actual value estimator (218) for extracting actual HR, BR and BP from sensed plurality of physiological data at the end of the activity performed by the subject;
        an actual RD value estimator (220) for estimating an actual recovery duration (RD) depending on the duration taken by the subject for recovery;
        a difference estimator (222) for estimating difference values between actual HR, BR, BP, RD and respective expected values of HR, BR, BP and RD;

a deviation estimator (224) for estimating a deviation factor based on the computed difference values and a pre-determined normalizing constant; and a classification module (226) for classifying the subject's fatigue as healthy or unhealthy fatigue based on the comparison of the deviation factor with a pre-determined standard value on the input/output interfaces (106).

9. The system of claim 8 further comprising longitudinal assessment module (228) for performing longitudinal assessment of estimated AI, nature of fatigue caused, and physiological sensor data continuously over several months to detect any underlying cardiopulmonary disorder.

10. The non-transitory computer-readable medium having embodied thereon a computer program to classify cardiopulmonary fatigue of a subject, comprising:

sensing a plurality of physiological data from the subject using a plurality of physiological sensors while the subject is performing an activity;

detecting a set of activity parameters using a plurality of activity detectors;

extracting initial heart rate (HR), breathing rate (BR) and breathing signal power (BP) from the sensed plurality of physiological data;

obtaining metabolic equivalent (MET) values from a MET database based on the activity performed by the subject during a pre-defined time interval, wherein the database stores MET values of multiple activities;

estimating activity intensity (AI) of the subject for the pre-defined time interval based on the MET values and the subject data;

estimating an expected value of HR, BR and BP based on estimated AI, initial HR, BR, BP and their respective pre-determined normalizing constant;

estimating an expected recovery duration (RD) based on estimated AI and its respective normalizing constant;

extracting actual HR, BR and BP from sensed plurality of physiological data at the end of the activity performed by the subject;

estimating an actual recovery duration (RD) depending on the duration taken by the subject for recovery;

computing difference values between actual HR, BR, BP, RD and respective expected values of HR, BR, BP and RD (320);

estimating a deviation factor based on the computed difference values and a pre-determined normalizing constant;

classifying the subject's fatigue as healthy or unhealthy fatigue based on the comparison of the deviation factor with a pre-determined standard value.

* * * * *